United States Patent
Shana'a et al.

(10) Patent No.: US 6,797,683 B2
(45) Date of Patent: Sep. 28, 2004

(54) ORDERED LIQUID CRYSTALLINE CLEANSING COMPOSITION WITH BENEFIT AGENT PARTICLES

(75) Inventors: May Shana'a, Trumbull, CT (US); Virgilio Barba Villa, Emerson, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 201 days.

(21) Appl. No.: 10/090,580

(22) Filed: Mar. 4, 2002

(65) Prior Publication Data

US 2003/0171231 A1 Sep. 11, 2003

(51) Int. Cl.[7] ............................................. C11D 17/00
(52) U.S. Cl. ...................................................... 510/370
(58) Field of Search ................................ 510/370, 158, 510/159

(56) References Cited

U.S. PATENT DOCUMENTS

| | | | |
|---|---|---|---|
| 5,849,105 A | * 12/1998 | Massaux et al. | 134/29 |
| 5,851,978 A | * 12/1998 | Shana'a | 510/417 |
| 5,932,528 A | 8/1999 | Glenn, Jr. et al. | |
| 6,066,613 A | 5/2000 | Tsaur et al. | |
| 6,270,836 B1 | 8/2001 | Holman | |

FOREIGN PATENT DOCUMENTS

| | | |
|---|---|---|
| EP | 0 686 386 A1 | 12/1995 |
| EP | 0 711 540 A1 | 5/1996 |
| EP | 1 063 007 A1 | 12/2000 |
| WO | 95/11000 | 4/1995 |
| WO | 97/05857 | 2/1997 |
| WO | 00/59454 | 10/2000 |
| WO | 01/70926 | 9/2001 |

OTHER PUBLICATIONS

*International Search Report PCT/EP 03/01693*, dated Jun. 24, 2003, 5 pp.
WPI Acc. No. 1996-021693/199603 Derwent Abstract of EP 0 686 386—2 pp.
WPI Acc. No. 1996-240449/199625 Derwent Abstract of EP 0 711 540—2 pp.
WPI Acc. No. 2001-149294/200116 Derwent Abstract of EP 1 063 007—2 pp.

* cited by examiner

Primary Examiner—John R. Hardee
(74) Attorney, Agent, or Firm—Alan A. Bornstein

(57) ABSTRACT

An ordered liquid crystalline phase cleansing composition is disclosed that contains particles with a structure comprising a benefit agent and a gellation agent and provides high foaming with in a preferred embodiment levels of free emollient equal to or in excess of the level of surfactant. A method of depositing a benefit agent to the skin or hair with the ordered liquid crystalline phase cleansing composition is also disclosed.

24 Claims, No Drawings

ORDERED LIQUID CRYSTALLINE CLEANSING COMPOSITION WITH BENEFIT AGENT PARTICLES

BACKGROUND OF THE INVENTION

1. Field of the Invention

The present invention relates to detergent compositions suitable for topical application for cleansing the human body, such as the skin and hair. In particular, it relates to ordered liquid crystalline phase compositions containing benefit agent particles.

2. Background of the Art

In order to be acceptable to consumers, a liquid personal cleansing product must exhibit good cleaning properties, must exhibit good lathering characteristics, must be mild to the skin (not cause drying or irritation) and preferably should even provide a benefit agent to the skin, such as an emollient. Several approaches have been used to provide high levels of benefit agents in a stable formula that have involved encapsulating the benefit agent which is then ruptured or dissolved with product use. For example, U.S. Pat. No. 5,932,528 to R. Glenn, Jr., et al. issued on Aug. 3, 1999 discloses a liquid cleansing composition containing a moisturizing phase comprising an encapsulated lipophilic skin moisturizing agent and an aqueous cleansing phase comprising a surfactant and a stabilizer. The encapsulated lipophilic skin moisturizing agent comprises a lipophilic skin moisturizing agent encapsulated within a complex coascervate comprising a polycation and a polyanion.

Other particles of material including microcapsules, bubbles, beads, ground particulates, and uniform particulates have been used in various cleansing and coating applications to encapsulate or bind the contents of various agents contained therein or associated therewith. For example U.S. Pat. No. 6,270,836 to Holman issued on Aug. 7, 2001 describes microcapsules coated with a gel, specifically a gel produced by the sol-gel process. The gel coating provides certain resistances to the microcapsules, resulting in enhanced protection for their contents. Microcapsules containing different types of materials are known which may be used as ingredients in the compositions of this invention, such as gelatin.

It is known that microcapsules may be formed by a coacervation or crosslinking process, in which lipids are coated by tiny droplets of proteins, carbohydrates, or synthetic polymers suspended in water. The process of coacervation is, however, difficult to control and depends on variables such as temperature, pH, agitation of the materials, and the inherent variability introduced by a natural protein or carbohydrate.

U.S. Pat. No. 6,066,613 to L. Tsaur, et al., issued on May 23, 2000; describes large hydrogel particles suspended in an aqueous medium and a continuous extrusion/mixing process for making this kind of hydrogel particles. The hydrogel particles comprise two different high molecular weight polymers. One is insoluble in the said aqueous medium and is used for network formation and gel integrity. The other is soluble in the said aqueous medium and helps control gel swellability and gel strength. Water insoluble materials are entrapped or encapsulated inside the network formed by these two polymers and are able to be more efficiently delivered from the aqueous composition (e.g., liquid cleanser containing the hydrogel particles). However there is no disclosure or suggestion in the prior art of an ordered liquid crystalline cleansing composition containing organogel particles wherein the particles are formed by associating benefit agents that are liquids at about 75 C with a gelation agent that is a solid at about 25 C and wherein said ordered liquid crystalline phase composition has a viscosity of about 40,000 to about 300,000 cps at 25 C.

BRIEF DESCRIPTION OF THE INVENTION

In one aspect of the present invention is an ordered liquid crystalline cleansing composition containing (a) about 3 to about 30% by weight of a surfactant system including at least one surfactant selected from an anionic, amphoteric, cationic and nonionic surfactant and mixtures thereof, wherein at least one anionic surfactant must be present (b) about 0.1% to about 15% by wt. of an ordered liquid crystalline phase inducing structurant; (c) about 0.1 to about 25% by weight of organogel particles of from about 0.05 to about 10 millimeters in diameter, the particle comprising a benefit agent that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C., and wherein said ordered liquid crystalline phase composition has a viscosity of about 40,000 to about 300,000 cps at 25 C.

In another aspect of the invention is a method for depositing a benefit agent on to the skin or hair with an ordered liquid crystalline phase cleansing composition, said composition comprising: (a) about 3 to about 30% by weight of a surfactant system including at least one surfactant selected from an anionic, amphoteric, cationic and nonionic surfactant and mixtures thereof, wherein at least one anionic surfactant must be present; (b) about 0.1% to about 15% by wt. of an ordered liquid crystalline phase inducing structurant; (c) about 0.1 to about 25% by weight of particles of from about 0.05 to about 10 millimeters in diameter, the particle comprising a benefit agent that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C.; and wherein said ordered liquid crystalline phase composition has a viscosity of about 40,000 to about 300,000 cps at 25 C.

Organogel particles suitable for the inventive cleansing composition comprise a hydrophobic (oleophilic) phase in particulate form, with no need for a rigid shell to encapsulate the phase, and usually with no shell present. The particle's oleophilic phase contains a gelation agent, and preferably an organogelation agent. Such particles have prolonged stability and can be simply manufactured. A preferred method of manufacture of the particles comprises forming a solution of at least the oleophilic material and gelation agent at a temperature above their gelation temperature, forming droplets of the solutions, and cooling the droplets to form particulates. Cooling may be effected by exposure to ambient conditions (e.g., room temperature) when the ingredients are appropriately selected with regard to their melting points, or an actual cooling environment may be needed to form the particles.

DETAILED DESCRIPTION OF THE INVENTION

For purposes of the present invention, the following definitions are used.

"gel" means a mixture of a solvent and solid material network (such as a solid network of particle network, fibroid network, reticulated network, and the like) wherein the solid material (e.g., any solid such as a waxy material, polymeric material, sintered or fused particle material, or any other solid material that forms a physically supportive network for the other component) is formed through physical aggregation of the solid material through any associative means. Generally, a gel is more viscous than a liquid or paste, and retains its shape when left undisturbed, i.e., is self-supporting. However, a gel is typically not as hard or firm as a wax. Gels may be penetrated more easily than a wax-like solid, where "hard" gels are relatively more resistant to penetration than "soft" gels. A rigid gel as defined herein resists deformation upon the application of a force.

"hydrogel" means a gel in which the solvent (diluent) is water or aqueous based liquids;

"organogel" means a gel in which the solvent (diluent) is an organic carrier or organic solvent (as opposed to water or aqueous based liquids);

"thermoreversible organogel" is synonymous with "physical organogel" and means an organogel whose network structure is due to weak, thermally unstable bonding such as hydrogen bonding (as opposed to strong, thermally stable bonds such as covalent bonds) and can, therefore, be heated to a free-flowing, liquid (molten) state. Upon cooling below a characteristic temperature ($T_{gel}$), the bonds reform and the solid-like gel structure is re-established.

$T_{gel}$ means a temperature at which, by any physical phenomenon, a mixture of ingredients (e.g., of an oil and organic material mixed therewith) in discrete form (e.g., particulate, droplet, drop, pastille, particle, thread, fibroid, etc.) passes from a flowable or liquid condition into a stable gel or semi-solid state. Usually this occurs by solidification of gelling or organization of a liquid material into a more solid form, adding structure to the discrete form.

In one aspect of the invention is an ordered liquid crystalline phase cleansing composition having:

(a) about 3 to about 30% by weight of a surfactant system including at least one surfactant selected from an anionic, amphoteric, cationic and nonionic surfactant and mixtures thereof, wherein at least one anionic surfactant must be present.
(b) about 0.1% to about 15% by wt. of an ordered liquid crystalline phase inducing structurant;
(c) about 0.1 to about 25% by weight of organogel particles of from about 0.05 to about 10 millimeters in diameter, the particle comprising a benefit agent, preferably an oleophilic substance that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C.
wherein said ordered liquid crystalline phase composition has a viscosity of about 40,000 to about 300,000 cps at 25 C.

Preferably the cleansing composition further includes about 1 to about 35% by weight of an emollient not bound to the particles (hereinafter "free emollient"). More preferably the cleansing composition includes about 10 to about 35% by weight of a free emollient wherein the level of emollient is equal to or in excess of the level of surfactant. Advantageously the inventive composition contains at least about 30% by weight water. Preferably the gelation agent includes an organic compound selected from a solid organic compound, a wax, and a polymer and the benefit agent includes an oil that is either a liquid or a solid at about 25 C. More preferably the cleansing composition includes about 0.1 to about 10% by wt. of organogel particles.

Advantageously the particle has an average diameter of between about 0.1 and about 3 millimeters and the proportions of the gelation agent to benefit agent are between about 0.5% to about 50% by weight gelation agent to benefit agent. Preferably the particle has an average diameter of between about 0.1 and about 1.0 millimeters and the proportions of the gelation agent to benefit agent are between about 0.5% to about 40% by weight gelation agent to benefit agent. More preferably, the particle has an average diameter of between about 0.1 and about 2 millimeters and the proportions of the gelation agent to benefit agent are between about 0.5% to about 30% by weight gelation agent to benefit agent.

Preferably the particle is aspherical, and the gelation agent forms a network of solid gelation agent within the particles formed of the benefit agent. Advantageously the particle contains a gradation of concentration of the gelation agent, with higher concentration of the gelation agent at the surface of the particles than at the core of the particles.

Advantageously the surfactant system is present at a concentration level of at least about 7% by weight and includes a mixture of anionic and amphoteric surfactants. Advantageously the composition includes about 10 to about 25% surfactant. Preferably the anionic surfactant is an alkali metal, C8–C16 ether sulfate, and the amphoteric surfactant is selected from an amphoacetate and an amidoalkyl betaine. Advantageously the ordered liquid crystalline phase inducing structurant is selected from a C8 to C24 alkenyl or branched alkyl fatty acid or ester thereof, a C8 to C24 alkenyl or branched alkyl alcohol or ether thereof, a C5 to C10 linear alkyl fatty acid, trihydroxystearin, and a mixture thereof, and the like.

Preferably the benefit agent is selected from vegetable oils, esters, animal fats, mineral oil, petrolatum, silicone oil and mixtures thereof and the like. More preferably the benefit agent is selected from sunflower seed oil, soybean oil, castor oil, almond oil, safflower oil, sesame oil, canola oil, jojoba oil and olive oil. Advantageously the inventive composition includes about 0.01 to about 3% by weight of a cationic polymer skin feel agent selected from cationic polysaccharides, cationic copolymers of saccharides and synthetic cationic monomers, synthetic cationic polymers, polymeric quaternary ammonium salts of hydroxyethylcellulose, cationic proteins, and salts and derivatives thereof, and the like.

The ordered liquid crystalline phase inducing structurant is preferably selected from lauric acid, oleic acid, palm kernel acid, palm fatty acid, coconut acid, isostearic acid, and mixtures thereof.

In another aspect of the invention is a method for depositing a benefit agent on to the skin or hair with an ordered liquid crystalline phase cleansing composition, said composition comprising:

(a) about 3 to about 30% by weight of a surfactant system including at least one surfactant selected from an anionic, amphoteric, cationic and nonionic surfactant and mixtures thereof, wherein at least one anionic surfactant must be present;
(b) about 0.1% to about 15% by wt. of an ordered liquid crystalline phase inducing structurant;
(c) about 0.1 to about 25% by weight of particles of from about 0.05 to about 10 millimeters in diameter, the particle comprising a benefit agent that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C.; and wherein said ordered liquid crystalline phase composition has a viscosity of about 40,000 to about 300,000 cps at 25 C.

Surfactants:

Surfactants are an essential component of the inventive cleansing composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The cleansing composition of the present invention contains one or more anionic detergents. The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

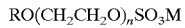
RO(CH$_2$CH$_2$O)$_n$SO$_3$M wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

R$^4$O$_2$CCH$_2$CH(SO$_3$M)CO$_2$M; and amide-MEA sulfosuccinates of the formula;

R$^4$CONHCH$_2$CH$_2$O$_2$CCH$_2$CH(SO$_3$M)CO$_2$M wherein R$^4$ ranges from $C_8$–$C_{22}$ alkyl and M is a solubilizing cation.

Sarcosinates are generally indicated by the formula:

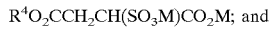
R$^1$CON(CH$_3$)CH$_2$CO$_2$M, wherein R$^1$ ranges from $C_8$–$C_{20}$ alkyl and M is a solubilizing cation.

Taurates are generally identified by formula:

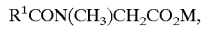
R$^2$CONR$^3$CH$_2$CH$_2$SO$_3$M wherein R$^2$ ranges from $C_8$–$C_{20}$ alkyl, R$^3$ ranges from $C_1$–$C_4$ alkyl and M is a solubilizing cation.

The inventive cleansing composition contains anionic surfactants, preferably $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

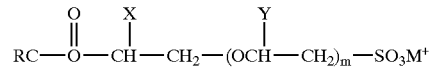

wherein R is an alkyl group having 8 to 18 carbons, m is an integer from 1 to 4, X and Y are hydrogen or an alkyl group having 1 to 4 carbons and M$^+$ is a monovalent cation such as, for example, sodium, potassium or ammonium.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

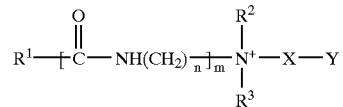

where R$^1$ is alkyl or alkenyl of 7 to 18 carbon atoms;

R$^2$ and R$^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —CO$_2$— or —SO$_3$—

Suitable amphoteric surfactants within the above general formula include simple betaines of formula:

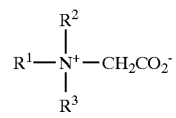

and amido betaines of formula:

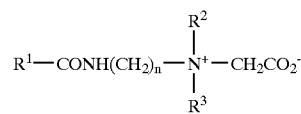

where n is 2 or 3.

In both formulae R$^1$, R$^2$ and R$^3$ are as defined previously. R$^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

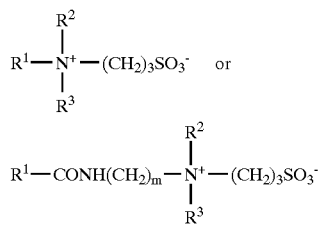

where m is 2 or 3, or variants of these in which $-(CH_2)_3SO_3^-$ is replaced by

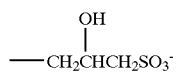

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the cleansing composition of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Cationic Surfactants

One or more cationic surfactants may also be used in the cleansing composition.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2',4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Humectants such as polyhydric alcohols, e.g. glycerine and propylene glycol, and the like; and polyols such as the polyethylene glycols listed below and the like may be used.

| | |
|---|---|
| Polyox WSR-205 | PEG 14M, |
| Polyox WSR-N-60K | PEG 45M, or |
| Polyox WSR-N-750 | PEG 7M. |

The benefit agent and free emollient may be the same or different. Furthermore the benefit agent or the free emollient or both may be a mixture of two or more compounds one or all of which may have a beneficial aspect. In addition, the benefit agent and free emollient may separately or together act as a carrier for other components one may wish to add to the cleansing composition.

A blend of a hydrophobic and hydrophilic emollients may be used. Preferably, hydrophobic emollients are used in excess of hydrophilic emollients in the inventive cleansing composition. Most preferably one or more hydrophobic emollients are used alone. Hydrophobic emollients are preferably present in a concentration greater than about 10% by weight, more preferably about 12% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters; magnesium, calcium, copper, zinc and other metallic components;

(l) sunscreens such as octyl methoxyl cinnamate (Parsol MCX) and butyl methoxy benzoylmethane (Parsol 1789);

(m) phospholipids;

(n) antiaging compounds such as alpha hydroxy acids, beta hydroxy acids; and (o) mixtures of any of the foregoing components, and the like.

Preferred benefit agents and free emollients are selected from triglyceride oils, mineral oils, petrolatum, and mixtures thereof. Further preferred benefit agents and free emollients are triglycerides such as sunflower seed oil.

Ordered Liquid Crystalline Compositions:

The inventive cleansing composition possesses ordered liquid crystalline microstructure, preferably lamellar microstructure structure. The Theological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical or ellipsoidal micelles may form. As surfactant concentration increases, ordered liquid crystalline phases such as lamellar phase, hexagonal phase, cubic phase or L3 sponge phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 issued to Puvvada, et al., on Sep., 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing ordered liquid crystalline dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring ordered liquid crystalline dispersions is using freeze fracture electron microscopy. Micrographs generally will show ordered liquid crystalline microstructure and close packed organization of the lamellar droplets (generally in size range of about 2 microns).

The inventive ordered liquid crystalline-isotropic composition preferably has a low shear viscosity in the range of about 40,000 to about 300,000 centipoises (cps) measured at 0.5 RPM using T-bar spindle A using the procedure described below. More preferably the viscosity range is about 50,000 to about 150,000 cps.

Organogels

A stable particle suitable for the inventive composition of from 0.05 to 2, 5 or 10 millimeters in diameter comprises a mixture of a benefit agent that is an oleophilic liquid at 25° C., 50° C., or 75° C. and a gelation agent or organogelation agent, the proportions of the gelation agent to oleophilic liquid being between 0.05% to 70%, or 0.05% to 50%, or 0.05% to 30% by weight gelation agent to oleophilic liquid, the $T_{gel}$ of the mixture being above 25° C. The gelation agent may comprise an organogelation agent, which is a term understood in the art and further defined herein. The particle may provide the oleophilic material liquid (or solid) as an oil, oil mixture, oil dispersion or suspension, or oil solution. A group of particles may have an average diameter of between 0.05 to 10 millimeters, between 0.08 and 10 millimeters, between 0.08 and 5 millimeters, between 0.1 and 5 millimeters, between 0.1 and 2 millimeters, and 0.1 and 1 millimeters and the proportions of the gelation agent to oleophilic liquid may be, for example, between 0.5% to 20% or more by weight gelation agent to oleophilic liquid.

The $T_{gel}$ of the mixture or the $T_{gel}$ of the individual components forming the organogel particle refers to the temperature at which the composition gels from an essentially liquid state as the temperature drops, or the temperature at which an individual component gels when the temperature of a liquid component is dropped.

A preferred method of forming such a stable organogel particle may include:

a) mixing together at least the oleophilic liquid and the gelation agent,
b) providing the mixture as a fluid material (having liquid or flowable properties), the mixture being at a temperature at least 5° C. above the solidifying temperature, such as at least 5° C. above the $T_{gel}$ of the mixture and/or the gelation agent;
c) forming discrete elements, such as droplets, pastilles, strands, particles, shapes, or other solid accumulations or gels of the material (preferably a fluid material); and
d) cooling the solid accumulation (e.g., droplets, strands, particles, shapes, etc.) to a temperature at or at least 5° C. below the solidification temperature of the gelation agent of the $T_{gel}$ of the mixture or gelation agent or at any other temperature that causes gelation to form solid, relatively stable particles.

Organogel particle hardness is an important parameter in formulating an acceptable cleansing composition. Typically the hardness is advantageously adjusted to be satisfactory to the user and can be defined as the Particle Breakage Index (PBI) or the amount of force (weight) required to break or rupture the particle. PBI is conveniently expressed in terms of grams per square millimeter and is calculated based on the following equation:

$$PBI = \text{weight need to break a particle } (g)/\text{cross section area of particle } (mm^2.)$$

Preferably, the particles should have a PBI value of about 0.05 up to 10, more preferably about 0.5 to about 5 and most preferably about 1.5 to 3.0. Such properties correspond to what the average user of the inventive cleansing composition considers as highly acceptable hardness for the particles. The strength can be controlled by the exercise of reasonable judgment and selection of ingredients and proportions according to art recognized techniques. Viscosity agents, thixotropic agents, surfactants, solid binders, antistatic agents, crosslinking agents, coupling agents, dispersing agents, emulsifying agents, thinning agents, and the like are among the types of additives that can be added in amounts between 0.001 and 30% by weight of the hydrophobic (oleophilic) material (e.g., the oil) to assist in the control of the properties of the organogel particles, such as size, physical strength, durability, and the like.

With respect to particle gel rheology, typically, gels possess a storage modulus G'(w) which exhibits a pronounced plateau at higher frequencies (on the order of 1–100 radians/second), and a loss modulus G"(w) which is considerably smaller than the storage modulus in the plateau region. In a strict sense, the term "gel" applies to systems having a value G'(w) that is higher than its value of G"(w) at low frequencies. Many of the compositions according to the present invention are gels by one or both of the above definitions. A gel is free-standing or self-supporting in that its yield value is greater than the shear stress imposed by gravity.

Rheological parameters such as the storage modulus G'(w) can be measured as a function of angular frequency with a parallel-plate rheometer. For example, such parameters can be generated using a Rheometrics Dynamic Analyzer Model 70, using a 0.5 cm stainless steel plate and a 2.3 mm sample gap, over a temperature sweep of 25–85° C. at 1% strain and 6.3 radians/sec. Characterization of the rheological behavior of a gelled body according to the present invention can be made using the Rheometrics instrument and conditions set forth above. As the gel is heated, it retains significant gel-like character until its Tgel temperature is reached. The viscosity of the particles at room temperature may typically vary from 10 to a few thousand cP or higher, even to the point of approaching properties that appear more solid than gel like.

Another property that may be directly measured is shear viscosity at e.g. 0.1 rad/sec as measured by ASTM D 2765-Procedure A. The shear viscosity, for example, may range from at least about 5 percent higher compared with the oil at room temperature to orders of magnitude higher than the shear viscosity at room temperature of the oils as measured by ASTM D 2765-Procedure A.

The precise process and phenomena that contribute to the formation of the particles, and the precise structure of the particles may vary between different combinations of materials, and even between different proportions of the same materials. It is believed that at least one of the following three systems and processes occur during the practice of the present invention, although these descriptions and/or hypothesis are not intended to be limiting on the scope of actual processes and structures that are provided in the practice of the present invention. The first method is where the two organic materials (the oleophilic agent and the gelation agent) are provided as a mixture at a temperature at which both materials are together as a fluid (e.g., preferably as a true liquid, but at least in a form that is flowable and in which the at least two ingredients are intimately mixed). This temperature usually requires that the softening temperature and/or the flow temperature or melt temperature (e.g., $T_{g1}$ and/or $T_{g2}$) be exceeded. After the fluid and the intermixed components have been provided at this elevated temperature (e.g., at a temperature above 25° C., above 40° C., above 50° C., above 60° C., above 75° C., above 85° C., above 100° C., above 120° C., above 150° C., above 175° C., and the like, up to temperatures short of where the individual components boil or decompose), the composition is cooled. The cooling temperature, depending upon how low a temperature to which the mixture is dropped, will cause at least one or both of the at least two ingredients to solidify. This cooling is done while the mixture is in or being placed into particulate form, as by prilling, pastilling, spray drying (or spray cooling in this case), or any other particle forming process. Because the at least two materials are intermixed, as opposed to the encapsulating relationship found in prior art microencapsulation processes, as the first or both at least two materials (the oleophilic agent and the gelation agent) harden or solidify, they remain intermixed. It is particularly at this point that the nature of the particle forming phenomenon becomes alternative in nature. The gelation agent, in some circumstances is believed to form fibroids, tendrils, fibers, reticulated structures, aspherical shapes, elongate elements or the like (e.g., with aspect ratios of at least 3, aspect ratios of at least 4 or 5, and higher, up to continuous filamentary elements with extremely high aspect ratios) within the particle material (e.g., within a droplet). These various structural elements form a physical support for the oleophilic material, whether supporting the oleophilic material by surface tension to the solid, adsorption to the solid, partial entrapment by the solid, entrapment by the solid, partial absorption by the solid, or by any other physical or physical chemical means by which the solid material supports and maintains a particulate shape for the at least two materials. A second method of stable particle, or droplet formation may occur where the structural elements may even be particulates without elongate structure (e.g., aspect ratios between 1 and 3, or between 1 and 5), wherein the physical forces between the particles and the oleophilic agent sustains the particle, or droplet structure. The particles may or may not be in contact with each other and may or may not be bound by physical or chemical means to each other during the gelation or solidifying process, but they do provide actual support for the particle, or droplet structure so that the product exists as a stable particle. A third method by which particle stabilization or gelation may occur is with the formation of a gradation of materials within the particle, with the highest concentration of the gelation agent at the surface of the droplet and the least concentration of the gelation agent (yet still above 0.0) occurring at center of the particle. This is not traditional encapsulation or microencapsulation where there is a clear distinction and sharp separation between a shell (solid) and a core (liquid). The gradation may have the outermost surface of the particle as 100% gelation material (and entrapped solids or intended diluents or active ingredients), but may also have 99%, 95%, 90%, 80%, 75%, 50%, 40%, 35% 30% or the like of gelation agent in the outermost surface and lower amounts within the body of the particle, the remainder of the concentration being provided as the oleophilic material and its associated components.

As noted above and later herein, a preferred aspect of the invention uses a gelation agent that is a solid at 25° C. to stabilize an oleophilic fluid, flowable or liquid material. The oleophilic material may also be a solid or difficult to flow material at 25° C., so that the particle may even be a solid oleophilic material in a solid matrix or network of solid supporting elements or gelation agent. The solid network of gelation agent may have provided structural support for the oleophilic material during the solidification process and remains as a network after the cooling of the oleophilic material to a solid. The final stable particle may therefore be a support system of the gelation agent and a liquid or semisolid or solid oleophilic material; in particle form. It must be noted again, that the term particle generically refers to a bead, pastille, solid droplet, fibroid, sphere, oblong, filamentary object, reticulated network, or other solid form with the required maximum diameter of 10 mm or less. The average diameter may be based upon number average diameter or any other basis as desired.

According to the present invention, molten (liquid) organogels are formed into any solid accumulation of materials such as droplets, particles, pastilles, strands, fibroids, from liquids provided above their gelation temperatures ($T_{gel}$). As is understood in the art, the $T_{gel}$ is the temperature at which gel-to-sol transition occurs. It is preferred that the $T_{gel}$ of the molten compositions be about between 20° C. and 70° C. when used to form the solid accumulations in forming the particles or the invention. It is also preferred that the molten coating compositions be coated from about 5C° to 25C° above the $T_{gel}$ of the composition.

The particle-forming compositions of the invention may also form thermoreversible gels, although any type of gel formation may be used. Generally, a thermoreversible organogel is characterized by the observation of a $T_{gel}$. The $T_{gel}$ may be determined by several different criteria, such as, for example, the temperature at which: (a) when a liquid composition is cooled, there is a rapid, discrete, qualitative change from liquid to solid properties; (b) when a liquid composition is cooled, there is a sudden increase in hydrodynamic radius, as measured by dynamic light scattering methods; (c) when a liquid composition is warmed, a 1 mm drop of mercury will flow through the composition; and (d) the elastic and viscous moduli are equivalent.

As noted above, the particles (which term is used to generically encompass the particles of the invention, whether they are beads, strands, particles, shapes, fibroids, filamentary shapes, pastilles or any other solid accumulation) are formed from two distinct materials that may be present as two distinct phases. The two distinct materials comprise what are referred to in the practice of the invention as the organic solid network, and the other component is referred to as the oleophilic liquid, oleophilic material or generally as the oleophilic organic medium. It may be difficult at times to distinguish which material is apparently working at the various function because of the dimensions and intimacy of the materials. For example, two phase or multiphase systems may form, or what is generally referred to as interpenetrating networks, where the functions of the materials, particularly where both materials may be present as solids, cannot clearly be defined or distinguished as a supporting, carrier, or supported phase. Even where a solid organic network is supporting a liquid organic medium, chilling the particle so that the liquid organic medium solidifies does not remove the particle from the practice of the invention. The gelation agent or organic solid network may be any organic material that passes from liquid to solid state during the cooling process and with its solid structure supports the other organic medium. The organic solid medium may comprise organic materials that are solids at the cool-down temperature, organic or inorganic waxes, polymers, copolymers, oligomers, and the like. The term gelation is used, rather than some other term, because the process appears to act in the manner of a gel-forming process, and many of the particles appear to act as gels, rather than solid particles.

The nature of some of the compositions, such as those that can be defined according to standards in the art as thermoreversible gels, are clearly gel and gelation compositions. Non-limiting examples of liquid compositions that form thermoreversible organogels at or near room temperature include nitrocellulose in ethyl alcohol, and the like. Although not wishing to be bound by theory, Applicants postulate that thermoreversible organogels suitable for use in the present invention may contain a polymer or copolymer wherein the polymer or copolymer chain contains two or more different functional groups or discrete regions, e.g., syndiotactic sequences prone to crystallite formation in a solvent or solvent mixture. It is believed that the addition of an alcohol to a polymer capable of hydrogen bonding prevents or reverses gel formation because of the hydrogen bonding of alcohol-based solvents with polymer sites capable of hydrogen bonding. The requirements of the solvent blend are that it must not interact with polymer hydrogen bonding sites along the polymer chain and thereby interfere with the polymeric binder's ability to undergo hydrogen bonding with itself through the such sites, yet it must solvate the polymer at the non-hydrogen bonding sites and be an overall solvent for the polymer at temperatures above $T_{gel}$. A further requirement is that upon cooling below $T_{gel}$ the polymer remains in solution forming a gel that is a homogeneous, clear, solid solution as opposed to forming an opaque heterogeneous mass.

In using molten thermoreversible organogel solutions, it is necessary to form the particles at temperatures above the $T_{gel}$ of the organogel. On the other hand, it is desirable to perform the processing at the lowest possible temperature above $T_{gel}$ in order to facilitate rapid onset of gelation after forming. It has been found advantageous to provide a "chill-box" or similar rapid chilling mechanism which functions immediately after the forming operation to trigger rapid gelation to inhibit interlayer mixing. Preferably, the molten organogel temperatures during forming should be 5C° to 25C° above $T_{gel}$. More preferably, the molten organogel temperatures during coating should be from about 10C° to about 15C° above $T_{gel}$.

The coating solutions or dispersions are solidified organogels at or near room temperature and liquids at a modestly elevated temperature. The solutions are warmed to 5C° to 25C° above their $T_{gel}$ so that they are liquids. The molten solutions are spray dried, prilled, pastilled, dispersion solidified, drip-dried, spray extruded, or as known by those of ordinary skill in the art to be otherwise formed into a solid particle by being cooled below their gel temperature while in particulate or droplet form.

The term "PLURONIC™" refers to poloxamer compounds useful as gelation agents and which are sold collectively under the trademark PLURONIC™ (BASF, Parsippany, N.J.). PLURONIC F-127 (PL 127) corresponds to poloxamer 407, a polyoxypropylene-polyoxyethylene block copolymer described by Schmolka in the Journal of Biomedical Materials Research 6:571–582, 1972. Other PLURONIC™ compounds may be used in the present invention. As used in this application, the terms PLURONIC™ organogel, poloxamer organogel, and polyoxyethylene/polyoxypropylene organogel are synonymous.

Other non-limiting examples of gelation materials include waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted) sugars, dibenzyl sorbitol (or mannitoal, rabbitol, etc.), condensates and precondensates of lower monohydric alcohols, trihydroic alcohols, lower polyglycols, propylene/ethylene polycondensates, and the like.

The benefit agent or oleophilic material may be any oleophilic material, whether a single pure compound, a solution, a composition, a mixture, an emulsion (e.g., an oil-in-water emulsion or preferably a water-in-oil emulsion), a dispersion, or the like. Among the many types of oleophilic materials useful in the inventive composition may be included oils, essential oils, emollients (as described above), antimicrobial agents, medications, exfoliating agents, fragrances, cosmetics, astringents, colorants, antioxidants, enzymes, sunscreens or ultraviolet radiation absorbing compositions, and the like. As noted the general range, when considering two phases, ranges from about 0.5% to 70% by weight of gelation agent and from 70 to 99.5% by weight liquid oleophilic composition. Alternative ranges of the gelation agent are from 1–60%, 1–50%, 1–30%, 2–25%, 5–25%, 7–25%, 10–25%, and 12–20% by total weight of the particle or by weight of the hydrophobic liquid. At the higher levels of gelation agent (e.g., from 12%–30%, greater than 15%, and from 15–30% by weight), the particles tend to be gelled more firmly, and are very stable, Benefit agents may be pure, raw, may contain dispersed materials or may have suspended or dispersed materials added to the benefit agent. For example, abrasive particles may be suspended to provide scrubbing or exfollient effects, silica, titania, calcium carbonate, talc, starch, pigments, conductive particles, reflective particles, frangible particles, reactive materials, moisture sensitive particles (e.g., urea particles, zeolites, gas-generating particles), and the like. Other forms of active or assistive ingredients are described elsewhere. The concentration of such materials may be from 0%, 0.001% to 20% or 40% of the hydrophobic component.

Various other ingredients, some of which have been noted above, may also be included within the solution prior to being formed into droplets. Such additional ingredients include (a) a wax or wax mixture of about 1 part by weight mineral ester wax having an acid value of about 0 to about 55, about 4 parts by weight partly saponified mineral ester wax having an acid value of about 10 to about 45, about 1.5 parts by weight insect wax having an acid value of about 0.2 to about 24; (b) a film-forming agent that is a curable material selected from the group consisting of a curable emulsion polymer, a curable resin, a curable aminofunctional silicone, and mixtures thereof; (c) a film-modifying agent that is a surfactant selected from the group consisting of a surface-active aminofunctional silicone, a linear arylalkyl modified polydialkyl siloxane, a linear alkylated copolymer of vinylpyrrolidone with a long chain ($C_{12}$ to $C_{22}$) alpha olefin, and mixtures thereof; (d) a nonionic emulsifying agent having an HLB* value of about 10 to about 15 and, for example, selected from the group consisting of an oil-soluble polyglycerol ester of a hydrophobic fatty acid capable of forming a water in oil emulsion, a water-soluble $C_8$ to $C_{18}$ alkylphenol ether with ethylene oxide having an average number of ethylene oxide units of of about 5 to about 70, and mixtures thereof (*HLB-hydrophile-lipophile balance); (e) an effective amount of an anionic oleophilic dispersing agent; (f) a thickening agent selected from the group consisting of polymers, colloids, alkaline earth metal aluminum silicate, non-ionic, cationic or anionic esters, and mixtures thereof; (g) an organic solvent selected from the group consisting of a liquid aliphatic hydrocarbon, a liquid aromatic hydrocarbon, and an oleoresinous liquid having an average kauri-butanol value above 50, and mixtures thereof; and (h) an effective amount of a preservative.

The properties of the particles may be controlled by various disciplines and additives as desired. The size can be controlled by the size of spray heads, the degree of shearing forces, the temperatures of the initial gel solution, the gelation rate, the viscosity of the gel composition, and other physical mechanisms.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLE 1

The following components were used to form an organogel particle suitable for the inventive cleansing composition.

| Sunflower oil | 89.5% |
|---|---|
| Polywax ® 500 | 10.0% |
| Pigment | 0.5% (Sun Chemical D&C Red #6 BA Lake) |

This formulation was combined and melted in a flask. The melted composition was then subsequently prilled into a water catch tank using a single fluid nozzle. Three different sized nozzles were used to produce particles that were approximately 600 to 800 microns, 800 to 1200 microns, and 1000 to 1400 microns.

The above particles of the size 800 to 1200 microns were placed in a gel consisting of: water, Vitamin E in SD alcohol 40, glycerin, polysorbate 20, aloe barbadensis gel, carbomer, triethenolamine, methyl paraben, imidazolidinyl urea, fragrance, Vitamin A palmitate, tea tree oil, colorants.

EXAMPLE 2

The following components were used to form an organogel particle suitable for use with the inventive cleansing composition.

Sunflower oil 80.9%

Fragrance oil 9.3

Intercontinental Fragrances Cinnamon Concentrate FG#8673

Polywax® 500 9.8

These ingredients were melted together and made into pastilles by depositing pasty droplets of materials onto a release surface and drying the droplets.

EXAMPLE 3

The following components were used to form an organogel particle suitable for use with the inventive cleansing composition. The firmness of sunflower oil gelled with 10% Polywax® 500 was compared with the firmness of sunflower oil gelled with 10% beeswax. It was found that the sunflower oil gelled with Polywax® 500 was firmer than sunflower oil gelled with beeswax.

EXAMPLE 4

The following kinds of organogel particles (a) to (f) suitable for use with the inventive cleansing composition were made:

| (a) | |
|---|---|
| Sunflower oil | 70% |
| Beeswax | 30% |
| (b) | |
| Sunflower oil | 70% |
| Carnauba wax | 30% |
| (c) | |
| Polywax ® 2000 | 10% |
| Sunflower oil | 90% |
| (d) | |
| Koster Kuenen Synthetic Paraffin Wax #201 | 5% |
| Sunflower oil | 95% |
| (e) | |
| Polywax ® 500 | 10% |
| Mineral Oil | 90% |
| (f) | |
| 90% AC Humko Cottonseed Flakes F05030 | |
| 10% Polywax ® 1000 | |

Blends (a) to (f) were separately melted and formed into pastilles.

EXAMPLE 5

The degree of softness and spreadablility as perceived with use of various inventive organogel particles was assessed according to test methods described below and the results are summarized in table 1.

TABLE 1

| Particle Composition | Particle Attributes | |
|---|---|---|
| Sunflower to Polywax Ratio | Degree of Softness | Ease of Spread |
| 80:20 | Very Hard | Unacceptable |
| 85:15 | Hard | Unacceptable |
| 90:10 | Just Right | Highly Acceptable |
| 94:6 | Soft | Slightly Acceptable |

EXAMPLE 6

Lamellar cleansing compositions I, II, and III were formulated as listed in table 1 and were evaluated for organogel particle stability and particle hardness:

Composition I was prepared by combining Sodium Lauroamphoacetate and Sodium Laureth Sulfate in a vessel, mixed and simultaneously heated to about 80 C until a clear solution was formed. Then Sodium Cocoyl Isethionate prills were mixed with the above surfactant solutions until dissolved completely, then opacifier, polymers citric acid and water were added to mixture. At this point, Cocamidopropyl Betaine was added to quench the mixture. The blend was then cooled down and during the cooling process, Dimethicone and preservatives were added. At about 40 C, isostearic acid was added to complete the structuring of the mix. When the temperature reached about 35 C fragrance was blended into the mix. Finally, after about 30 minutes of mixing, the organogel particles were mixed with the final blend. Composition II was prepared similarly as I, except that sunflower seed oil was used in lieu of dimethicone, and Sodium Cocoyl Isethionate was replaced with Cocamide MEA. Also, sunflower seed oil was pre-blended with glycerin, and isostearic acid and added at about 40 C.

Composition III was prepared slightly differently from compositions I and II. Initially sunflower seed oil, PEG-30 Dipolyhydroxystearate, Lanolin Alcohol, cocamide MEA, petrolatum and lauric acid were mixed together in a resin kettle at about 80 C until a homogenous clear blend is formed. Then, glycerin was added and at that point the blend was allowed to cool down. Subsequently, cocamidopropyl betaine and sodium laureth sulfate were added and mixed until the blend achieved homogenous consistency. Thereafter, water, Guar Hydroxypropyltrimonium Chloride, citric acid, titanium dioxide EDTA, EHDP and preservative were added. When the batch cooled down to about 35 C, perfume was added and finally once the final blend became homogenous, the organogel particles were added and mixed. The viscosity of the resulting composition was about 90,000 cps.

The composition of the organogel particles was about 98% sunflower seed oil and Polywax 500 blend at an 80:20 ratio and the remaining 2% balance consisted of pigment colorants. The average particle size was determined to be about 1200 microns.

Assessment of product stability for composition III was done by visual assessment based on 2-phase separation of the base and particles creaming to the top. Results of the product stability evaluation revealed no signs of product separation nor accumulation of particles on the surface of the base. The finished products were visually stable, i.e., particles did not exhibit any signs of rising to the top and remained uniformly distributed throughout the base.

TABLE 2

| | % Active Level in Formula | | |
|---|---|---|---|
| Chemical Name | I | II | III |
| Sodium Lauroamphoacetate | 5.6 | 10.0 | — |
| Cocamidopropyl Betaine | 6.0 | 1.9 | 5.7 |
| Sodium Cocoyl Isethionate | 6.5 | — | — |
| Sodium Laureth Sulfate | 6.5 | 13 | 12.3 |
| Cocamide MEA | — | 2.0 | 1.9 |
| Lauric Acid | — | — | 2.8 |
| Glycerin | — | — | 5.7 |
| Petrolatum | — | — | 3.7 |
| Lanolin Alcohol | — | — | 0.5 |
| Isostearic Acid | 5.0 | 3.0 | — |
| Sunflower Seed Oil | 0.25 | 7.5 | 21.3 |
| Dimethicone (60,000 cst) | 5.0 | — | — |
| Polyquaternium 37/Propylene Glycol Dicaprylate/Dicaprate/PPG-1 Trideceth 6* | 0.25 | — | — |
| Citric Acid | 1.0 | 1.7 | 0.1 |
| Propylene Glycol | 0.5 | — | — |
| PEG-30 Dipolyhydroxystearate | — | — | 0.25 |
| Polyquaternium 39 | 0.1 | 0.1 | — |
| Guar Hydroxypropyltrimonium Chloride | 0.1 | 0.25 | 0.7 |
| Organogel Particle | 2 | 2 | 1 |
| Opacifier/Colorant | 0.2 | 0.2 | ~0.1 |
| Perfume/Preservative | 1.25 | 1.2 | 1.2 |
| Diluent/Water to | 100.0 | 100.0 | 100.0 |

*Trade Name is Salcare SC-96

Stability findings was consistent on all products that were stored under the following accelerated aging conditions:

1. 51.7 C for a period of 1 month
2. 40.5 C for a period of 1 month
3. −9.5C/25 C—3 complete cycles where 1 cycle constitute 23.5 hours under −9.5 C followed by another 23.5 hours under 25 C
4. 40.5 C/25 C—3 complete cycles Stability evaluation is performed visually by comparing the samples stored under accelerated conditions and the control sample (stored under 25 C)

EXAMPLE 7

Organogel particles of the composition given in table 3 were made according to the following procedure: All three samples were spray chilled (prilled) using a pressure pot and single fluid nozzle. The orifice diameter used in samples A and B was 0.020 inches and the orifice diameter of the nozzle used in sample C was 0.028 inches. The material was melted and the pot was heated to keep the material above 105 degrees C. The pressure used to prill sample A and B was 20 psi and the pressure used to prill C was 40 psi.

TABLE 3

| Sample | Composition | Sample Size, n (number of particles tested) | Mean Diameter, (microns) | Mean Weight to Break Particle (g) | Mean PBI (Particle Breakage Index, g/mm2) |
|---|---|---|---|---|---|
| A | Sunflower Oil 89.96% Polywax 500 9.99% Pigment* 0.05% | 15 | 742.90µ ± 40.26 | 3.2 g ± 0.68 | 1.9 |
| B | Sunflower Oil 79.92% Polywax 500 19.98% Pigment* 0.10% | 15 | 773.30µ ± 64.74 | 12.9 g ± 2.6 | 6.9 |
| C | Sunflower Oil 93.54% Polywax 500 5.96% Pigment* 0.50% | 31 | 1184.2µ ± 193.2 | 0.77 g ± 0.51 | 0.2 |

Sun Chemical Light Rubine Lake)

Methods:
Particle Breakage Index (PBI)

A microscope, a microscope slide and a microscope coverslip are required. A coverslip is placed on top of the slide. A single particle is obtained from the sample and placed on top of the coverslip. Using the microscope and a 10×objective, the diameter of the particle is measured. After measuring the particle, another coverslip is placed on top of the particle. Sufficient weight is placed on top of the coverslip until the particle ruptures. The weight required to rupture the particle is recorded. Cross sectional area of the particle is estimated as $A=\pi r^2$, where r is the radius of the particle.

Particle Stability

Particle Stability may be shown when the rate of particles rising/floating ('creaming') to the top is very low. This rate is measured by Stoke equation:

$$V_s = \frac{2r^2 g(\sigma - \rho)}{2\eta_o}$$

where
  r=particle radius, m
  g=acceleration due to gravity, 9.807 m/sec$^2$
  σ=density of suspending medium, kg/m$^3$
  ρ=density of particle, kg/m$^3$
  $\eta_o$=zero shear viscosity, kg/m-sec
  $V_s$='creaming' rate, m/sec Perceived Organogel Particle Softness/Hardness and Ease of Spreadability During Use.

Panelists pour organogel (about 10 to 20) particles between the thumb and either the index and/or middle finger and press them gently between the fingers until the particles rupture. The panelist then rate the particles' degree of softness/hardness based on the following rating scale—Very Hard, Hard, Just Right, Soft and Very Soft. Then the panelists squeeze the ruptured particles in circular motion between fingers.

To assess the particles' ease of spreadability, a small amount of sample (about 10 to 20 particles) is poured onto the back of one of the palms of a panelist. Then these particles are squeezed gently, using forward and backward motions, against the back of the palm with the middle finger and/or the index finger of the other hand. Once the particles are completely spread over the back of the palm, the panelist will rate them for ease of spreadability using the following scale: Unacceptable, Slightly Acceptable and Highly Acceptable.

T-Bar Viscosity Measurement
Scope:

This method covers the measurement of the viscosity of the ordered liquid crystalline cleansing composition.

Apparatus:
  Brookfield RVT Viscometer with Helipath Accessory;
  Chuck, weight and closer assembly for T-bar attachment;
  T-bar Spindle A;
  Plastic cups diameter greater than 2.5 inches.

Procedure:

1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.

4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.
6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial reading by a factor of 4,000 and report the viscosity reading in cps.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. An ordered liquid crystalline phase cleansing composition comprising:
   (a) about 3 to about 30% by weight of a surfactant system including at least one surfactant selected from an anionic, amphoteric, cationic and nonionic surfactant and mixtures thereof, wherein at least one anionic surfactant must be present;
   (b) about 0.1% to about 15% by wt. of an ordered liquid crystalline phase inducing structurant;
   (c) about 0.1 to about 25% by weight of organogel particles of from about 0.05 to about 10 millimeters in diameter, the particle comprising a benefit agent that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C.; and
   wherein said ordered liquid crystalline phase composition has a viscosity of about 40,000 to about 300,000 cps at 25 C.

2. A composition according to claim 1 further comprising about 1% to about 35% by weight of a free emollient wherein the level of the emollient is equal to or in excess of the level of surfactant.

3. A composition according to claim 1 further comprising greater than about 30% by weight water.

4. A composition according to claim 1 wherein the gelation agent comprises an organic compound selected from a solid organic compound, a wax, and a polymer.

5. A composition according to claim 1 wherein the benefit agent comprises an oil that is a liquid at about 25 C.

6. A composition according to claim 1 wherein the benefit agent is a solid at about 25° C.

7. A composition according to claim 1 wherein the ordered liquid crystalline phase cleansing composition is a lamellar composition.

8. A composition according to claim 1 wherein the particle has an average diameter of between about 0.1 and about 3 millimeters and the proportions of the gelation agent to benefit agent are between about 0.5% to about 50% by weight gelation agent to benefit agent.

9. A composition according to claim 1 wherein the particle has an average diameter of between about 0.1 and about 1.0 millimeters and the proportions of the gelation agent to benefit agent are between about 0.5% to about 40% by weight gelation agent to benefit agent.

10. A composition according to claim 1 wherein the particle has an average diameter of between about 0.1 and about 2 millimeters and the proportions of the gelation agent to benefit agent are between about 0.5% to about 30% by weight gelation agent to benefit agent.

11. A composition according to claim 1 wherein the particle is aspherical.

12. A composition according to claim 1 wherein the gelation agent forms a network of solid gelation agent within the particles formed of the benefit agent.

13. A composition according to claim 1 wherein the particle contains a gradation of concentration of the gelation agent, with higher concentration of the gelation agent at the surface of the particles than at the core of the particles.

14. A composition according to claim 1 wherein the surfactant system is present at a concentration level of at least about 7% by weight.

15. A composition according to claim 1 wherein the surfactant system includes a mixture of anionic and amphoteric surfactants.

16. A composition according to claim 3, wherein the anionic surfactant is an alkali metal, C8–C16 ether sulfate, and the amphoteric surfactant is selected from an amphoacetate and an amidoalkyl betaine.

17. A composition according to claim 1 wherein the ordered liquid crystalline phase inducing structurant is selected from a C8 to C24 alkenyl or branched alkyl fatty acid or ester thereof, a C8 to C24 alkenyl or branched alkyl alcohol or ether thereof, a C5 to C10 linear alkyl fatty acid, trihydroxystearin, and mixtures thereof.

18. A composition according to claim 1 wherein the benefit agent is selected from vegetable oils, esters, animal fats, mineral oil, petrolatum, silicone oil and mixtures thereof.

19. A composition according to claim 1 further comprising about 0.01 to about 3% by weight of a cationic polymer skin feel agent selected from cationic polysaccharides, cationic copolymers of saccharides and synthetic cationic monomers, synthetic cationic polymers, polymeric quaternary ammonium salts of hydroxyethylcellulose, cationic proteins, and their salts, derivatives and mixtures thereof.

20. A composition according to claim 5, wherein the benefit agent is selected from sunflower seed oil, soybean oil, castor oil, almond oil, safflower oil, sesame oil, canola oil, jojoba oil olive oil and mixtures thereof.

21. A composition according to claim 5, wherein the ordered liquid crystalline phase inducing structurant is selected from lauric acid, oleic acid, palm kernel acid, palm fatty acid, coconut acid, isostearic acid, and mixtures thereof.

22. A composition according to claim 1, comprising about 10 to about 25% surfactant.

23. A method for depositing a benefit agent on to the skin or hair with an ordered liquid crystalline phase cleansing composition, said method comprising the steps of:
   1. Providing an ordered liquid crystalline phase cleansing composition comprising:
      (a) about 3 to about 30% weight of a surfactant system including at least one surfactant selected from an anionic, amphoteric, cationic and nonionic surfactant and mixtures thereof, wherein at least one anionic surfactant must be present;

(b) about 0.1% to about 15% by wt. of an ordered liquid crystalline phase inducing structurant;

(c) about 0.1 to about 25% by weight of particles of from about 0.05 to about 10 millimeters in diameter, the particle comprising a benefit agent that is a liquid at about 75° C. and a gelation agent that is a solid at about 25° C., the proportions of the gelation agent to benefit agent being between about 0.05% to about 70% by weight gelation agent to benefit agent, the solidification or gelation temperature of the mixture being at or above about 25° C.; and wherein said ordered liquid crystalline phase composition has a viscosity of about 40,000 to about 300,000 cps at 25 C.

2. Topically applying the cleansing composition to the skin or hair; and

3. Rubbing the particles on the skin until the particles rupture and release the benefit agent contained therein.

24. The method of claim 23 wherein the ordered liquid crystalline phase cleansing composition is a lamellar composition.

* * * * *